United States Patent [19]

Lontz

[11] Patent Number: 5,644,032

[45] Date of Patent: Jul. 1, 1997

[54] PROCESS FOR PRODUCING FIBRINOGEN CONCENTRATES

[75] Inventor: John F. Lontz, Wilmington, Del.

[73] Assignee: Fibrin Corporation, Wilmington, Del.

[21] Appl. No.: 391,277

[22] Filed: Feb. 21, 1995

Related U.S. Application Data

[63] Continuation of Ser. No. 221,183, Mar. 31, 1994, abandoned, which is a continuation-in-part of Ser. No. 44,585, Apr. 8, 1993, Pat. No. 5,420,250, which is a continuation-in-part of Ser. No. 855,752, Mar. 23, 1992, abandoned, which is a continuation-in-part of Ser. No. 759,698, Sep. 9, 1991, abandoned, which is a continuation-in-part of Ser. No. 562,839, Aug. 6, 1990, abandoned.

[51] Int. Cl.$^6$ .............................. C07K 1/14; C07K 1/30; C07K 14/75

[52] U.S. Cl. .......................... 530/382; 530/427; 530/830; 530/418

[58] Field of Search ............................ 530/381, 382, 530/383, 384, 412, 414, 418, 427, 830

[56] References Cited

U.S. PATENT DOCUMENTS

| | | | |
|---|---|---|---|
| 2,492,458 | 12/1949 | Bering et al. | 530/382 |
| 3,523,807 | 8/1970 | Gerendas et al. | 106/124 |
| 4,251,437 | 2/1981 | Rasmussen et al. | 530/383 |
| 4,278,592 | 7/1981 | Seufert et al. | 530/382 |
| 4,289,691 | 9/1981 | Rock et al. | 530/383 |
| 4,298,598 | 11/1981 | Schwarz | 514/2 |
| 4,359,049 | 11/1982 | Redl et al. | 604/82 |
| 4,362,567 | 12/1982 | Schwarz et al. | 106/157 |
| 4,377,572 | 3/1983 | Schwarz et al. | 514/2 |
| 4,414,976 | 11/1983 | Schwarz et al. | 530/362 |
| 4,427,650 | 1/1984 | Stroetmann | 530/382 |
| 4,600,574 | 7/1986 | Lindner | 424/448 |
| 4,608,254 | 8/1986 | Philapitsch | 424/530 |
| 4,627,879 | 12/1986 | Rose et al. | 106/124 |
| 4,631,055 | 12/1986 | Redl et al. | 604/82 |
| 4,650,678 | 3/1987 | Fuhge et al. | 514/2 |
| 4,735,616 | 4/1988 | Eibl | 604/191 |
| 4,909,251 | 3/1990 | Seelich | 606/213 |
| 4,928,603 | 5/1990 | Rose et al. | 106/124 |
| 4,960,757 | 10/1990 | Kumpe et al. | 514/21 |
| 5,321,126 | 6/1994 | van Dommelen et al. | 530/380 |
| 5,420,250 | 5/1995 | Lontz | 530/381 |

FOREIGN PATENT DOCUMENTS

WO8601814 3/1986 WIPO.

OTHER PUBLICATIONS

Anonymous, Freezing and Thawing Serum Cells, Technical Bulletin, *Art to Science*, vol. 5, No. 2, HyClone Laboratories, Logan, Utah. 1986.

ASTM Designation D–413—82 Standard Test Methods for Rubber Property—to Flexible Substrate, pp. 70, 71, 73 and 74. 1990.

ASTM Designation F–639—79:85 Standard Specification for Polyethylene Plastics for Medical Applications, p. 164, 1990.

ASTM Designation D–638—68 Standard Method of Test for Tensile Properties of Plastics, pp. 189, 195–197, 1990.

Brands et al., Preservation of the Ruptured Spleen by Gluing with Concentrated Fibrinogen. Experimental and Clinical Results. *World J. Surg.*, vol. 6, 1982 366–368.

Brodniewicz–Proba et al., Modified Glycine Precipitation Technique for the Preparation of Factor VIII Concentrate of High Purity and High Stability Vox–Sang 1987 52:10–14.

Castillo et al., Prothrombin Times and Clottable Fibrinogen Determination on An Automated Coagulation Laboratroy. *Thrombosis Res.*, 1989 213–219.

Cohn et al., Preparation and Properties of Serum and Plasma Proteins. IV. A system for the separation into fractions of the protein and lipoprotein components of biological tissues and fluids *J. Am. Chem. Soc.* 68:459–475. 1946.

Conte et al., Infection–Control Guidelines for Patients with the Acquired Immunodeficiency Syndrome (AIDS), *The New Eng. Jour. of Med* 1983 740–744.

Dresdale et al., Hemostatic Effectiveness of Fibrin Glue Derived from Single–Donor Fresh Plasma. *Ann. Thor. Surg.* 1985 40:385–387.

Dresdale et al., Preparation of Fibrin Glue from Single–Donor Fresh–frozen Plasma, *Surgery* 1985 97:750–754.

Edsall et al., Effects of Ions and Neutral Molecules on Fibrin Clotting *J. Biol. Chem.* 1951 191:735–756.

Epstein, et al., Current Safety of Clotting Factor Concentrates *Arch. Pathol. Lab. Med.* 1990 114:335–340.

Espstein, G. H. et al., A New Autologous Fibrinogen–Based Adhesive for Otologic Surgery. *Ann. Otol. Rhinol Laryngol,* 1986 95:40–45.

Fennema, O., Behaviour of Proteins at Low Temperatures. Food Protein Preservation. Mechanism and Funtionality. *Am. Chem. Soc.* Series 209, 1982 109–135.

Farrugia et al., "Studies on the procurement of blood coagulation factor VIII effects of plasma freezing rate and storage conditions on cryoprecipitate quality", *J. Clin. Pathol.* 1985 38:433–437.

*FDA Drug Bulletin* vol. 8, No. 2, pp. 15–16, Mar. Apr. 1978.

Gestring, Gidon F., Autologous Fibrinogen for Tissue–Adhesion, Hemostasis and Embolization Vascular Surgery 1982 294–296, and 303.

Grey, R.G. Fibrin as a Hemostatic in Cerebral Surgery. *Surg. Gynecol. Obstr.* 1915 21:452–454.

Holmes et al., Studies of a–Proteins in Human Cell Cult., *In Vitro,* 1979 15:522–530.

Klein, J., The Interdiffusion of Polymers, *Science,* 1990 250:640–641.

Kram, H.B., et al., "Fibrin Glue Sealing of Polyetetrafluoroethylene Vascular Graft Anastomoses. Comparison with Oxidized Cellulose", *J. Vascular Surgery,* 1988, 8:563–568.

Putnam, Frank W., Ed. *The Plasma Proteins,* Ch. 2. vol. 1, Pennell, Robert B. Fractionation and Isolation of Purified Components by Precipitation Methods, pp. 9–50 1960.

Putnam, F.W., Ed. *The Plasma Proteins, 2nd Ed.,* Section 3. Doolittle, R.F., Fibrinogen and Fibrin pp. 108–160, 1975.

Putnam, F.W., Ed. *The Plasma Proteins, 2nd Ed.,* Section 4. Clamp, J.R. Structure and Functions, pp. 136–141, 163–211, 1975.

Siedentop et al., Autologous Fibrin Tissue Adhesive, *Laryngoscopy,* 1985 95:1074–1076.

Spotnitz et al., Fibrin Glue from Stored Human Plasma, *The American Surgeon* 1987 No. 8:460–462.

Cucuianu et al. Rev. Chir. Oncol. Radiol. O.R.L. Oftalmol. Stomatol. Sec. *Oto–Rino–Laringologia* 1988 33:81–88 and English Translation.

Lozina–Lozinski, Studies in Cryobiology, 195–203 John H. Wiley & Sons, New York. (No date).

The Lancet, issued 01 Jul. 1978, Mason, "Thaw–Siphon Technique for Production of Cryoprecipitate Concentrate of Factor VIII", pp. 15–17.

*Primary Examiner*—Jeffrey E. Russel
*Attorney, Agent, or Firm*—Fish & Richardson P.C.

[57] ABSTRACT

A process for producing a fibrinogen concentrate for use as a tissue adhesive from mammalian plasma includes freezing the plasma to a temperature of at most about −20° C. for less than four hours in a container having a surface to volume ratio of from about 4.38:1 to about 1.65:1 reciprocal centimeters, thereby producing frozen plasma; thawing the frozen plasma at a temperature of at least about 4° C. for a time sufficient to attain about 5% to about 95% residual icing, thereby producing thawed plasma; and centrifuging the thawed plasma to produce a fibrinogen concentrate having a solids content of about 6% to about 44% solids by weight of the concentrate.

18 Claims, 4 Drawing Sheets

PROCESS FOR PRODUCING FIBRINOGEN CONCENTRATES

REFERENCE TO RELATED APPLICATIONS

This application is a continuation of Ser. No. 08/221,183, filed Mar. 31, 1994, now abandoned, which is a continuation-in-part of Ser. No. 08/044,585, filed Apr. 8, 1993, now U.S. Pat. No. 5,420,250, which is a continuation-in-part of Ser. No. 07/855,752, filed Mar. 23, 1992, now abandoned, which is a continuation-in-part of Ser. No. 07/759,698, filed Sep. 9, 1991, now abandoned, which is a continuation-in-part of Ser. No. 07/562,839, filed Aug. 6, 1990, now abandoned. This application is related to Ser. No. 08/220,815, which was filed concurrently with this application on Mar. 31, 1994.

BACKGROUND OF THE INVENTION

Fibrinogen is one of the numerous proteins of blood plasma from which the phenomena and mechanisms emanate to form the structure of the fibrin clot. Its ubiquitous physiological role in internal restructuring or repair of tissue discontinuity has been extended to a corresponding role of external application developed over the past scores of years as a concentrate processed from plasma for tissue bonding under such descriptive terms as fibrin glue, fibrin adhesive, fibrin weld, fibrin sealant, and so on.

The clinical use of fibrin prepared from plasma by various methods of cryoprecipitation and chemical insolubilization has gradually emerged for such early uses as a hemostyptic adhesive powder with small open vessels (Berger, 1909), as a hemostatic agent in cerebral surgery (Grey, 1915), in suturing of peripheral nerves (Matras et al, 1972), and gradually expanding to the repair of traumatized tissues (Brands et al, 1982), and the anastomoses or restructuring of cardiovascular, colon, bronchial sections, severed nerve endings, and other anatomical discontinuities currently in wide-spread practice often replacing or augmenting conventional suturing. In such clinical applications, the native fibrinogen content in human plasma averages 513 milligrams per deciliter (mg/dcl) according to standard clinical assays, and ranges from 229 mg/dcl to 742 mg/dcl standard deviation, based on photometric measurements of turbidity from clotting (Castillo, 1989). This range of native concentration, corresponding to 0.229% to 0.742% (averaging 0.531%) of the human population, is too dilute and too fluid with the aqueous burden being principally water, for direct application to tissue site for direct or assisted bonding.

The separation and/or concentration of fibrinogen emanated from precipitation using concentrated salt solutions, such as semi-saturated sodium chloride (Hamerstein, 1878) and saturated ammonium sulfate, cold (−3° C.) ethanol (Cohn et al. 1946), other low molecular weight organic liquids (Pennell, 1960) and amino acids (Edsall and Lever, 1951), and numerous combinations of these precedent precipitations. These procedures, using excessive osmolal additives based on physicochemical gradations of solubility, were applied to the preparation of high purity, single fibrinogen protein entities stripped of the natively associated proteins, notably glycoproteins and other peptides, for analytical and molecular characterization.

The clinical preparations of cryoprecipitation at the −80° C. range have been applied from at least 6 hours (Gestring, 1982) to the general practice of 24 hours (Dresdale et al, 1985; Spotnitz et al, 1987); in another instance, plasma was "deep frozen" at −18° C. for 72 hours presumably with a longer time to compensate for the difference to the lower cryogenic precipitation. In none of these general practices has there been any indication of the concentrate yield or product characterization and quality. All of these preparations require prolonged preparation times.

The thawing time in numerous known, published methods has not been consistent and in no instances related to either the quantity or quality of the attained fibrinogen concentrates. For instance, the thawing time may vary from such indefinite temperature-time kinetics as at 4° C. "when liquid" (Gestring, 1982), for "several hours" at 4° C. (Dresdale, 1985a), after slow rethawing at 4° C. (Dresdale, 1985b), slowly thawed at 1° C. to 60° C. for 20 hours (Siedentop, 1985), and also at 1° C. to 60° C. for 12 hours; in no instance has there been any indication of yield, solids content, or clinical assay of the fibrinogen content. In all these instances prolonged thawing with re-dissolving of the cryoprecipitates during the temperature-time thermal drift, lead to inordinate loss of fibrinogen and its associated proteins with solids contents varying from as little as 3% to 6%; the factor ($\times$) of concentrating efficiency based on initial 0.531% fibrinogen amounts to only 5.9$\times$ to 11.7$\times$.

The current practices of centrifugation involve a wide range of speed (RPM), gravitational force ($\times$g), temperatures, and time. These include, for instance, unspecified cold centrifuge at 2300 g for 10 to 15 minutes (Gestring, 1982), thawed cryoprecipitate at 1000$\times$ g for 15 minutes (Dresdale 1985), 1° C. to 6° C. at 5,000 rpm (unspecified $\times$g) for 5 minutes (Siedentop, 1985), room ambient temperature at 10.000$\times$ g for 20 minutes (Epstein, 1986), and 4° C. at 6500$\times$ g for 5 minutes (Spotnitz, 1987). The last named is the only source that provided a yield averaging 11.7 ml of fibrinogen concentrate from 250 cc plasma with a calculated solids content of 3.9%.

The present state of the art in applying reproducible engineering processing components as a system of integrated temperature time kinetics is not only confusing and completely devoid of corresponding overall temperature time force controls but also completely lacking in relating the kinetics to process efficiency in terms of the yields and assay of the derived fibrinogen protein concentrates.

Therefore, a process for preparing fibrinogen concentrates having a higher level of solids content with specified and defined specifications is needed for the ever increasing clinical demand for fibrinogen and related clottable factors (Epstein et al., 1990). Furthermore, this need is cogent not only for large scale production from pooled blood fractions but particularly for small lot ready preparation of fibrinogen concentrate from autologous patient plasma in view of the prevalent risks of viral infection, notably numerous forms of hepatitis and particularly human immunodeficiency virus, from pooled or single donor sources. In addition, small packaged lots may be prepared by the process of the present invention for use in emergencies.

SUMMARY OF THE INVENTION

The present invention is directed to a process for producing a fibrinogen concentrate from mammalian plasma comprising freezing said plasma to a temperature of at most about −20° C. for less than four hours, thereby producing frozen plasma; thawing said frozen plasma at a temperature of at least about 4° C. for a time sufficient to attain from about 5% to about 95% residual icing, thereby producing thawed plasma; and centrifuging said thawed plasma to produce a fibrinogen concentrate having about 6% to about 44% solids content.

The objective of this invention is to provide an integrated process engineering system for producing high yields of cryoprecipitation and assay of fibrinogen concentrates with optimum temperature time constants in each of the integral process steps of cryoprecipitation, thawing, and centrifugation.

Another objective is to provide a process of making a fibrinogen concentrate comprising a substantial proportion of associated plasma proteins.

Still another objective is to provide a simple procedure of determining the solids content of the cryoprecipitates. A simple analytical method for determining the total and varied protein content in the control of the engineering processing constants for maximum efficiency in producing fibrinogen concentrates from plasma is also provided.

Still another objective is to provide engineering processing temperature time constants for the integrated preparation of high concentration fibrinogen product, including an autologous product, within the time frame of two to four hours in contrast with the prolonged schedules practiced in the current state of the art.

These and other objectives as described or implied are further provided in the ensuing descriptive details and examples.

BRIEF DESCRIPTION OF THE DRAWINGS

FIG. 3 reveals enhanced yields of the fibrinogen concentrates with a substantial decrease in processing time.

DETAILED DESCRIPTION OF THE INVENTION

The present invention is directed to a process for producing a fibrinogen concentrate from mammalian plasma comprising freezing said plasma to a temperature of at most −20° C. for less than four hours, thereby producing frozen plasma; thawing said frozen plasma at a temperature of at least about 4° C. for a time sufficient to attain from about 5% to about 95% residual icing, thereby producing thawed plasma; and centrifuging said thawed plasma to produce a fibrinogen concentrate having about 6% to about 44% solids content.

The freezing step of the present invention subjects the plasma to a temperature below the freezing point of the plasma. The temperature for freezing mammalian plasma in the process of the present invention is at most −20° C., more preferably about −20° C. to about −120° C., even more preferably about −80° C. Freezing may be performed for less than about four hours, more preferably about 0.5 hours to about 4 hours, even more preferably about 1 hour. At these temperatures, the plasma is frozen to temperatures which compact the concentrate thereby making it more dense.

Thawing for purposes of the process of the present invention takes place at a temperature of less than about room temperature, more preferably from about 4° C. to about 10° C., even more preferably about 4° C. The thawing step of the present invention is performed for a time range of from about one hour to about 30 minutes. The time and temperature of the thawing step of the process of the present invention are performed such that from about 5% to about 95% residual icing, more preferably about 30% to about 95% residual icing, even more preferably about 30% to about 40% residual icing is formed.

The process of the present invention may be depicted as follows:

| Process phases | | |
|---|---|---|
| cryoprecipitation | → thawing 0° C. | → centrifugation |
| (solidus) | (de-icing) | (liquidus) |

For small lot clinical preparations of blood fractions from single donor lots of blood, the cryoprecipitates are thawed and then centrifuged to separate specific fractional products generally in a closed system to avoid environmental contamination using blood collection kits in conformity with standards prescribed by the American Association of Blood Banks. In bulk large scale processing of pooled lots of blood, appropriate form and means of containment against environmental contamination are likewise provided for in similar processing stages or steps of cryoprecipitation, thawing, and centrifugation. Containers for use in the methods of the present invention preferably have a surface: volume ratio of about 4.38:1 to about 1.65:1 reciprocal centimeters ($cm^{-1}$).

Cryoprecipitation is used as the initial, principal means of separating fibrinogen in preference to the herein mentioned plasma solids. It is minimally chemically reactive or disturbing to the intricate native configuration of the plasma proteins. Unlike lyophilization, cryoprecipitation does not remove water from the plasma. Accordingly, hydrogen bonds are not broken in the cryoprecipitate and thus, water need not be added to reconstitute it as is required by some conventional products. Surprisingly, cryoprecipitation in itself has not been adequately explored or studied in the kinetic temperature-time precipitation along with the thermal drift in relation to cooling rates and thawing rates. Considering the presence of hundreds of protein components in plasma of varying rates of insolubilization to the cryogenic temperature and the reverse of re-solubilization, the thermal drift in each direction provides the arena for limiting the nature and constitution of the fibrinogen concentrate.

Cryoprecipitation is therefore a preferable means of producing the fibrinogen concentrate over the alternative of precipitation with adjunctive non-physiological chemical precipitants such as saturated salts, low molecular weight organic fluids or organic compounds that are suspect of imposing major physical, conformational changes in the molecular form and shape of the fibrinogen structures (Doolittle, 1975a). Although cryoprecipitation is not in itself without some imposition of structural changes, it can be reasonably conjectured that the transition to and from cryogenic temperatures through the icing stage under restrictions of the temperature-time kinetics avoids the potentially drastic chemical environment on the extremely sensitive component chain linkages and their resistance to fibrinolysis (Doolittle, 1975b).

However, as is generally the inevitable phenomenon of continued chemical activity in the cryogenic state (Fennema, 1982) of native proteins, particularly that of associated enzymes and possibly fibrinolytic activity, the unduly prolonged cryogenic state in terms of the kinetic temperature-time factor has not been defined in the conventional practices of preparing fibrinogen concentrates. A critical feature of the invention is the discovery of cryoprecipitation and its hitherto nonobvious effects on yield and components of the cryoprecipitated fibrinogen concentrates. None of the currently available methods and preparations would be deemed acceptable for immediate clinical autologous usage in 2 to 4 hours.

Following the cryoprecipitation process step, thawing is the next essential and critical component of the process of the present invention. During thawing, the solid heterogeneous crystalline-like mush transforms into two phases of a viscous fluid with a glacialized homogeneous solid ice progressively melting with the thermal drift at thawing. The thermal drift is critical to the concentrate yield, the solids concentration, and the distribution of the numerous proteins through the solidus—liquidus equilibrium temperature. During thawing/de-icing, the frozen solid plasma releases the insoluble fibrinogen and innumerable associated proteins that are important for fibrinogen concentrates or more properly termed fibrinogen protein concentrates depending upon the attained purity of the fibrinogen concentrates. The latter is the ratio of the fibrinogen associated proteins which can be regulated by the thermal drift of the solidus to liquidus transition as the more soluble associated proteins re-dissolve in time. These include a range of bioadhesives (Gurny and Junginger, 1990) characteristic of the mucoproteins, chemically known as glycoproteins which are indigenous to fibrinogen, and are also intended to be retained as much as possible within the purview of the present invention. The thawing is readily evident from the progress of de-icing and thereby regulated by selected time and temperature. Thus, thawing retains the useful and/or valuable plasma proteins natively associated with the complex structures of fibrinogen.

By applying a specified critical control at the deicing or thawing stage of the solid cryoprecipitate to the liquid watery state, throughout the time of continued thermal drift to and from cryofreezing, the new processing system results in considerably higher yields and solids contents of the fibrinogen protein concentrate with a diversity of the associated useful protein contents. Thermal drift refers to the temperature differences between the external thermal exposure and internal thermal plasma states during the three processing stages of minimally adjusted, time sparing, cryoprecipitation, thawing, and centrifugation. The overall process efficiency is thereby markedly and unexpectedly increased and processing time considerably shortened from the starting plasma to the separated fibrinogen concentrate.

The retention of the associated proteins is highly dependant upon the thermal drift from the cryogenic state through icing equilibrium to centrifugation by means of minimal time in the liquidus watery phase at which the associated proteins begin and continue to dissolve.

Following thawing, the cryoprecipitate is then subjected to the physical separation by centrifugation as the continuation of the temperature time frame of thermal drift but with the minimal centrifugation time frame and with specified gravitation force at stated revolutions per minute (RPM). Minimizing the temperature time thermal drift presents a critical process intermediary to assure maximizing the yield of the clinically useful fibrinogen.

Solidus-liquidus equilibrium transition temperature is a temperature at which, for each component of the solids content of the fibrinogen concentrate, the solid (i.e. ice or frozen) phase and liquid phase of a component are in equilibrium. For example, the solidus—liquidus equilibrium transition temperature for water is the temperature at which ice and liquid water exist in a percent ratio of about 50:50. Residual icing refers to the amount of solid phase, i.e. ice, as compared to the components which have passed through the transition temperature into the liquid phase. Thawing permits each of the component parts of the plasma to reach a transition temperature such that the components pass from the solid phase to the liquid phase. By controlling the solidus-liquidus transition with time and temperature in the thawing step, the residual icing is thereby controlled. Control may similarly be established where thawing and centrifuging occur at the same time.

Residual icing appears in the form of ice. In examples set forth herein, test tubes were used as a containment such that residual icing formed as ice plugs.

$$\text{Residual icing} = \frac{\text{weight or volume of ice plug}}{\text{weight or volume of initial plasma}} \times 100$$

Following determination of the weight of residual icing by weighing, the percent residual icing may be readily estimated visually. Visual estimation proved workable in Table 2 below in a range from 10% to about 100% residual icing.

Centrifugation is performed to produce a fibrinogen concentrate having about 6% to about 44% solids content, more preferably about 24% solids content and even more preferably 12% solids content. Centrifuging may be performed at a gravitational force of about 8000× g to about 1450× g, for about thirty minutes to one hour, respectively.

The invention is directed to a method of making cryoprecipitated native, undenatured, non-lyophilized fibrinogen concentrates. The fibrinogen concentrates of the present invention may be associated with nascent indigenous proteins and enhanced solids content for viscous adhesion in tissue bonding.

The present invention is directed to a method of making a cryoprecipitated fibrinogen concentrate of native mammalian plasma comprising about 6% to about 44% solids content, wherein about 5% to about 95% is clottable fibrinogen, said cryoprecipitate having a viscosity of from about 80 to about 430 centipoises, and a tensile break force of about 1 to about 8 lb-f/in-w.

The solids content of the fibrinogen concentrate comprises components in the molecular weight range of from about 18 including salts and electrolytes; to about 8,000 to 600,000 Daltons including fibrinogen and associated amino acids and proteins including and not limited to albumin, mucoproteins, Factor XIII, fibronectin, plasminogen, prothrombin, thrombin, and other proteins including and not limited to growth factors, and the like. The remaining 94% to 56% of the concentrate is water and other liquids associated with plasma. The transition temperature varies for each of the component parts of the solids content of the fibrinogen concentrate. As the thawing time decreases, residual icing increases.

The present invention may be performed using mammalian plasma including and not limited to human, bovine, porcine, rabbit, and ovine plasma. Human plasma for use in the present invention may be allogenic or autologous. Any of the mammalian plasmas may also be cryoprecipitated together with any of the associated proteins identified above. For example, albumin may be combined with plasma, wherein the ratio of plasma to albumin is from about 100:0. 90:10. 80:20, and 60:40. Further, the supernatant remaining from plasma which has been passed through one cycle of cryofreezing, thawing, and centrifuging, may be reused or recycled to further prepare a cryoprecipitate therefrom. Pooled cryoprecipitates from several sources and/or processes are also within the scope of the invention. Pooled cryoprecipitate may also result from various processes or repeated processes with variations in time, temperature, cryofreezing, thawing, and centrifuging. The process of the present invention may be repeated for a plurality of times such that a plurality of supernatants and a plurality of concentrates are produced. The supernatant may be recycled through the process again for a number of times to provide a plurality of concentrates. The concentrates may then be combined for use as a sealant.

Mammalian plasma or cell plasma and modifications thereof with supplemental additions and inclusions of various kinds are within the scope of the present invention. Modifications and/or supplemental additions may include coprecipitants that induce precipitation of associated plasma proteins, or similar molecular or biologically active entities, for conversion of the concentrates to new products for specific uses. These include such common modifications as (a) anticoagulants including ACD citrate or heparin, (b) anti-fibrinolytic agents such as aprotonin, and epsilon-aminocaproic acid, (c) coagulating agents such as calcium compounds, (d) viscosifying and thixotropic modifiers either naturally occurring or synthetic polysaccharides, mucopolysaccharides, and polygalacturonic acid, (e) bioadhesives in the form of mucoproteins or glycoproteins indigenous to plasma or serum or their synthetic analogs, (f) surfactants such as naturally occurring mucoproteins and mucopolysaccharides of the N- or O- substituted neuraminic acids, (g) supplementing with precipitating agents affecting the electrolyte balance and/or osmolality of the plasma such as ethanol, urea, glycine, and their homologous chemical structures, and (h) preservatives of choice against bacterial or microorganism activity.

Supplementation of the fibrinogen protein concentrate may be carried out in several ways, including and not limited to adding supplements to the initial plasma and then processing them together or by supplementing the fibrinogen concentrate after processing.

In order to establish productivity, defined qualification tests, and standards lacking in the prior art, a novel and more efficient process engineering system was devised as herein described. A substantially higher level of solids content within the fibrinogen concentrate was achieved by applying a controlled thermal drift throughout the integrated cryoprecipitation, thawing, and centrifuging steps. In addition, the overall processing time is also shortened over that described in the prior art. The qualifications provided by the product of the present invention, serve as a basis for specifications for clinically safe and effective enhanced fibrinogen concentrate products for large scale production from pooled plasma and for limited small scale lots of enhanced autologous fibrinogen concentrates from patients in view of the prevalent risks of viral infections, notably numerous forms of hepatitis and human immunodeficiency virus (HIV), from pooled or single-donor sources.

EXAMPLE I

This example illustrates the marked improvement and process innovation in the critical role of cryoprecipitation by reducing the prolonged time of 6 to 72 hours (Gestring, 1982; Siedentop, 1985; and Dresdale, 1985) in cryofreezing commonly used in preparing fibrinogen concentrates. Such reduction in time is highly important, particularly for single donor and autologous readiness in urgent, ready clinical need. In this example, the prolonged times of other preparations were reduced to a progressive time series of ½, 1, 2, and 4 hours. This is a major change over the prescribed prolonged times, preparation of the considered adequate for the preemptive needed fibrinogen concentrate, especially in an emergency. All plasma transfers from single donor collections into centrifuging tubes throughout all of the Examples were carried out under air sterile certified biological safety cabinets using surgical glove protection against viral infection.

Forty milliliters of frozen (fresh or stored, −20° C.) human plasma was placed in a sterilized 50 ml polypropylene centrifuge tube (Gibco, Bethesda, Md.) providing a 1.65 surface volume ratio, an important factor in thermal transfer of the thus contained plasma during cryofreezing and thawing steps of the process. The higher this ratio, the higher the rate of the thermal transfer or thermal drift, during freezing, thawing, and centrifuging.

Cryoprecipitation. A centrifuge tube of the 40 ml plasma was subject to cryofreezing at −80° C. for 0.5 hours and promptly transferred intact to next process operation. Cryoprecipitation at −80° C. was repeated for three additional time periods: 1.0, 2.0, and 4.0 hours, hereinafter also referred to as individual timed series.

Thawing. Following each of the individual timed series of the preceding cryoprecipitation the solid plasma in the form of dispersed loose crystals of ice slush was thawed in a constant temperature incubator at 37° C. for 30 minutes. The thawing step of the present invention is another major reduction from published practices ranging from 12 hours at 1° C. to 6° C. (Spotnitz, 1987) to indefinite or non-indicated periods (Dresdale, 1985; Lupinetti, 1985), as "completely liquid" (Gesting, 1982). On completion of this temperature-time schedule of thawing, each time tube of plasma was then transferred to the next process step of centrifuging at the icing solidus—liquidus stage for controlled de-icing.

Centrifuging. The thawed series tubes of plasma were centrifuged at a constant 2000 RPM speed (1450× g) at the refrigeration temperature of 4° C. for a constant period of 30 minutes. Following the completion of this process, the sedimented fibrinogen content was freed of the fluid spent plasma by careful decanting. The sedimented concentrate is subjected to quantitative materials accounting or balance based on yield of the concentrate and the corresponding solids content on dry basis for a standardized clinical assay as milligrams per deciliter (mgm/dcl) as normally applied to the clinical fibrinogen assay. In this regard, it is most surprising that the currently available methods of preparing fibrinogen for clinical applications provide neither the yield nor the solids content for which the ensuing method has been purposely devised. Thus, the present invention is the standard in developing high fibrinogen concentrates from the complete process engineering of this invention.

Solids Content. The method of the present invention is based on the evaporation of the fibrinogen yield at 100° C. in an air circulating oven in a progressive time series to a constant residual weight.

Figure 1:
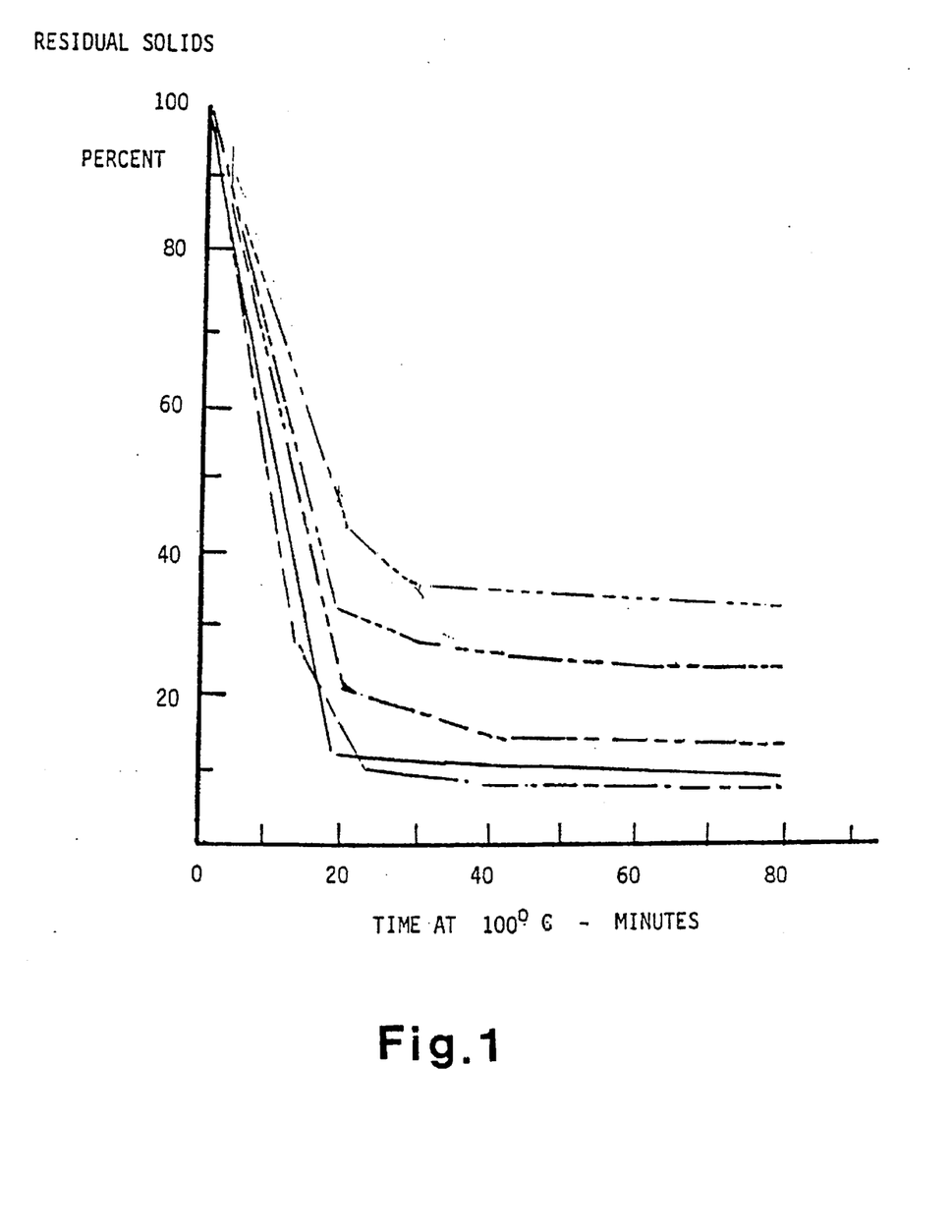
FIG. 1 depicts a plot of the percent solids content versus evaporating time at 100° C. of the fibrinogen concentrate sample to constant dry weight on a dimensionally prescribed evaporating surface.

A sample of the fibrinogen concentrate yields weighed to 1.0±0.1 grams was placed in a 1-inch square 4-mil thick aluminum pan with a ¼ inch wall and an evaporating surface of 6.45 square centimeters. The pan was easily constructed from a 1.5 inch square aluminum sheet from which the ¼ inch walls are formed by 90° folds edgepinched over a square inch form of ¼ inch thick acrylic sheet. With the appropriate tare and gross weights, the pan is placed in the air oven set to 100° C. for 80 minutes. FIG. 1 indicates a typical plot of the residual solids to constant weight in the form of a thin brittle film. The residual dry concentrate comprises fibrinogen with associated plasma proteins, the contents of which can be determined by usual analytical methods and, as indicated in a succeeding example, by means of polyacrylamide gel electrophoresis.

Effect of cryofreezing time. Table 1 summarizes the effect of the incremental series of cryofreezing time at ½, 1.0. 2.0, and 4 hours on the concentrate product yields processed for the first time, see Fraction I. Fraction II represents the results from a second cycle of the process of freezing, thawing, and centrifuging, using the spent (decanted) supernatant plasma from the first Fraction I with the same incremental cryofreezing time.

Fraction I. In this first Fraction I cryoprecipitation series, the yields ranging from 1.021 to 0.914 grams, and percent solids from 12.4 to 13.0 indicated no difference in the effectiveness of reduced cryofreezing time of 0.5, 1.0, 2.0, and 4.0, and hence no need for extending to the conventional 16 to 72 hours. The slightly higher 30 minute yield, approximately 10% higher, than that of the other three extended cryofreezing times is normal for the process variation. This can also be concluded for the percent solids content averaging 13.1% (SD ±0.62, ±4.7%) which provided a concentration 25.6 times (×) that of the initial plasma, averaging 0.531% fibrinogen by clinical assay (Castillo, 1989). This is compared to the prior art range of 3.0 to 6.0% solids content with a corresponding concentrating (×) range of only 5.9× to 11.7× obtained according to one of the published cryoprecipitation and thawing procedures (Gesting, 1982). This is clearly a surprising discovery, and indicative of the enhanced process efficiency of this invention in reducing substantially the excessive cryofreezing period of 6 to 72 hours to 1 hour and the excessive thawing time as much as 16 hours to one-half hour compared to other reported preparations of fibrinogen concentrates. It is a noteworthy quality feature not indicated in the prior art that the higher 13.1% solids of this Example is a more viscous concentrate, measured in relation to the viscosity of glycerol, compared to the watery 3.6% to 9.0% concentrates of the prior art which require re-cooling to increase the viscosity for adherence and handling in surgical applications.

Fraction II. Since the extent to which cryoprecipitation and the applied thawing and centrifugation completely exhausts separation of the fibrinogen from the plasma has not been established by any prior art, a second cryoprecipitation into Fraction II was carried out with the same temperature time thawing and centrifugation as in the Fraction I using the spent supernatant plasma from Fraction I. This was also undertaken on the presumption that the thawing at 37° C. for 30 minutes may have redissolved some of the cryoprecipitate and thereby complexed the overall process kinetics of the temperature time variables and reduced the process efficiency. In this second Fraction II series as shown in Table 1, the gram yield of 0.522 gram at 30 minutes cryofreezing doubled to 1.051 grams with 4 hours cryofreezing with irregular trends in percent solids averaging 17.0% (SD±1.48) which provides a still higher 33.2× concentrating efficiency over that attained in the preceding Fraction I which may be due to some undetermined transient ambient thermal irregularity or drift. As made evident in an ensuing example the fibrinogen concentrate is actually a complex fibrinogen protein concentrate, the two terms being used synonymously in reference to the redissolving of the associated proteins.

TABLE 1

Effect of Cryofreezing Time Protein Concentrate Summary from Two-Stage Cryoprecipitation Process

|  | TUBE NUMBER | | | |
|---|---|---|---|---|
|  | 1 | 2 | 3 | 4 |
| Fraction I Cryofreezing | | | | |
| Temp (°C.) | −80 | −80 | −80 | −80 |
| Time (hrs) | 0.5 | 1.0 | 2.0 | 4.0 |
| Thawing | | | | |
| Temp (°C.) | 37 | 37 | 37 | 37 |
| Time (hrs) | 0.5 | 0.5 | 0.5 | 0.5 |
| Centrifuging | | | | |
| Temp (°C.) | 4 | 4 | 4 | 4 |
| Time (mins) | 0.5 | 0.5 | 0.5 | 0.5 |
| Yield | | | | |
| grams | 1.021 | 0.927 | 0.922 | 0.914 |
| % solids | 12.4 | 12.9 | 13.9 | 13.0 |
| Fraction II Cryofreezing | | | | |
| Temp (°C.) | −80 | −80 | −80 | −80 |
| Time (hrs) | 0.5 | 1.0 | 2.0 | 4.0 |
| Thawing | | | | |
| Temp (°C.) | 37 | 37 | 37 | 37 |
| Time (hrs) | 0.5 | 0.5 | 0.5 | 0.5 |
| Centrifuging | | | | |
| Speed (rpm) | 2000 | 2000 | 2000 | 2000 |
| Temp (°C.) | 4 | 4 | 4 | 4 |
| Time (min) | 0.5 | 0.5 | 0.5 | 0.5 |
| Yield | | | | |
| grams | 0.522 | 0.865 | 0.867 | 1.051 |
| % solids | 16.1 | 19.0 | 15.8 | 17.0 |
| Total Yield grams | 1.543 | 1.792 | 1.859 | 1.965 |
| *Concentrated Factor | 7.26x | 8.44x | 8.75x | 9.25x |

*Based on fibrinogen universal mean ($\mu$) 531 mgm/decl.

EXAMPLE II

This example illustrates the importance of controlling the thermal drift during the thawing process and during the centrifugation which have not hitherto been made evident from any of the prior art. In particular it is intended to demonstrate the importance of maintaining the minimum of thermal drift above the icing stage. In this example the Du Pont RC–3C Sorvall Low speed clinical centrifuge was used with a HG–4L swinging bucket with four polypropylene carriers (Du Pont, Wilmington, Del.) to carry 16 mm×100 mm polypropylene tubes. Each tube contained 9 ml units of plasma in quadruplicates for fractional runs designated Fraction I, II, etc. for a range of progressive, usually doubling, increasing centrifuging time phases designated 1, 2, 3, etc. in minutes. The 9 ml plasma unit provided a surface:volume ratio of about 4.65:1 reciprocal centimeters, capable of providing a more efficient thermal transfer compared to the surface:volume ratio of 1.65:1 reciprocal cm, with the 40 ml plasma units used in the tubes in previous Example I. The thermal drift was thereby increased during the thawing and centrifuging by 2.8 fold. The thermal drift can be expected to vary somewhat with different centrifuge manufacturer's designs especially in regard to refrigeration, speed, and dimensions of the different rotor systems, such as provided in this and other examples. These critical design features have not been described or unequivocally specified in any of the prior art and therefore account for the variability noted in the reported preparations and applications in the surgical use and handling of fibrinogen concentrates. The processing elements or stages of this example are specified as follows.

Cryofreezing. The cryoprecipitation was standardized at −80° C. for 1 hour for each of the quadruplicate 9 ml units of plasma for the subsequent three phases of the incremental time range of thawing. The units in plastic tubes were spaced in a completely open wire test tube rack and separated by about half-inch to allow thorough and uniform cryofreezing.

Thawing. Following cryofreezing the plasma units were thawed in two series of schedules, namely, Series A as the continuation of the previously described accelerated thawing at 37° C. with progressively decreased thawing time; and Series B eliminating altogether the accelerated 37° C. temperature. Illustrating these two series of increasing thawing are the external thermal profiles FIG. 2 and FIG. 3 as typical examples for Series A and Series B, respectively affecting the product yields and per cent solids as summarized in Table 2 for the complete process engineering system. In both Series, the thawing was supplemented with a procedural standby of approximately 30±5 minutes at 0° C. and at transient room temperature initially required for incidental procedural set up time such as indexing the multiplicity of tubes, decanting, etc. These steps were eliminated altogether in the continued development of high efficiency centrifugation process and product program illustrated by one of succeeding examples.

Centrifuging. In this Example, the centrifuging speed was fixed to 4000 RPM (1970× g) with progressively increasing time phases of 10, 20, 40, and 60 minutes at refrigeration temperature of 4° C. determined on the basis of gradual decrease in the transition icing with some retention of the solidus to liquidus state at about 0° C., the freezing temperature of the plasma.

The purpose of this gradual de-icing at the solidus—liquidus state of equilibrium, heretofore not known nor made evident in the prior art, is first to direct the precipitation from the crystalline solidity to the liquidus state near or at 0° C., and second to avoid or minimize the redissolving of the fibrinogen and the more soluble associated plasma glycoproteins, Factors II, IV, VIII, and XIII, growth factors, and other components that are naturally present and highly necessary in the clinical applications of the plasma fibrinogen for use as a bioadhesive and in wound healing.

While the control refrigeration was set at 4° C. maximum, the internal centrifuge air refrigerating reading was at 2° C. to 3° C. The internal temperature in the solidus—liquidus transition state was at 0° C. with as little as 10% residual icing. This does not imply any discrepancy as the single control refrigeration temperature takes into account its location and the influence of the metal mass, to which the refrigeration usually over-responds, while the internal plasma content is shielded by the insulating effect of the polypropylene carrier with the very evident icing following the completion of each of times series. The centrifuge setting, in this example at 4° C., either higher or lower, will depend upon the refrigeration efficiency coordinated with temperature control and in turn to the mass and velocity of the centrifuging load. With one or more trial runs, these can be readily determined for the most efficient yield of the fibrinogen concentrates.

Figure 2:
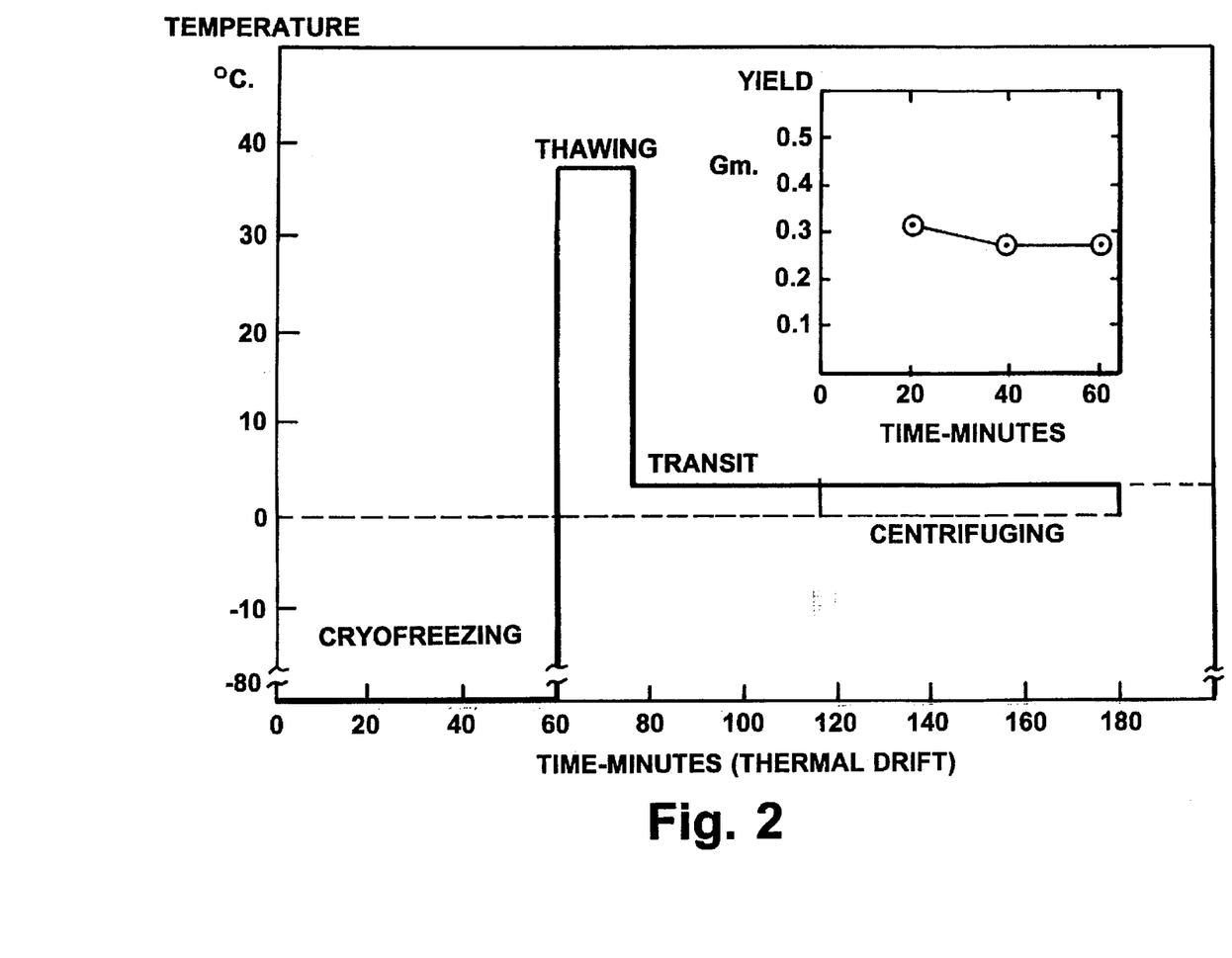
FIG. 2 exhibits a graph of thermal drift temperature versus time during the three process stages of freezing, thawing, and centrifuging with corresponding yields of the fibrinogen concentrate at three progressive centrifuging times.
Figure 3:
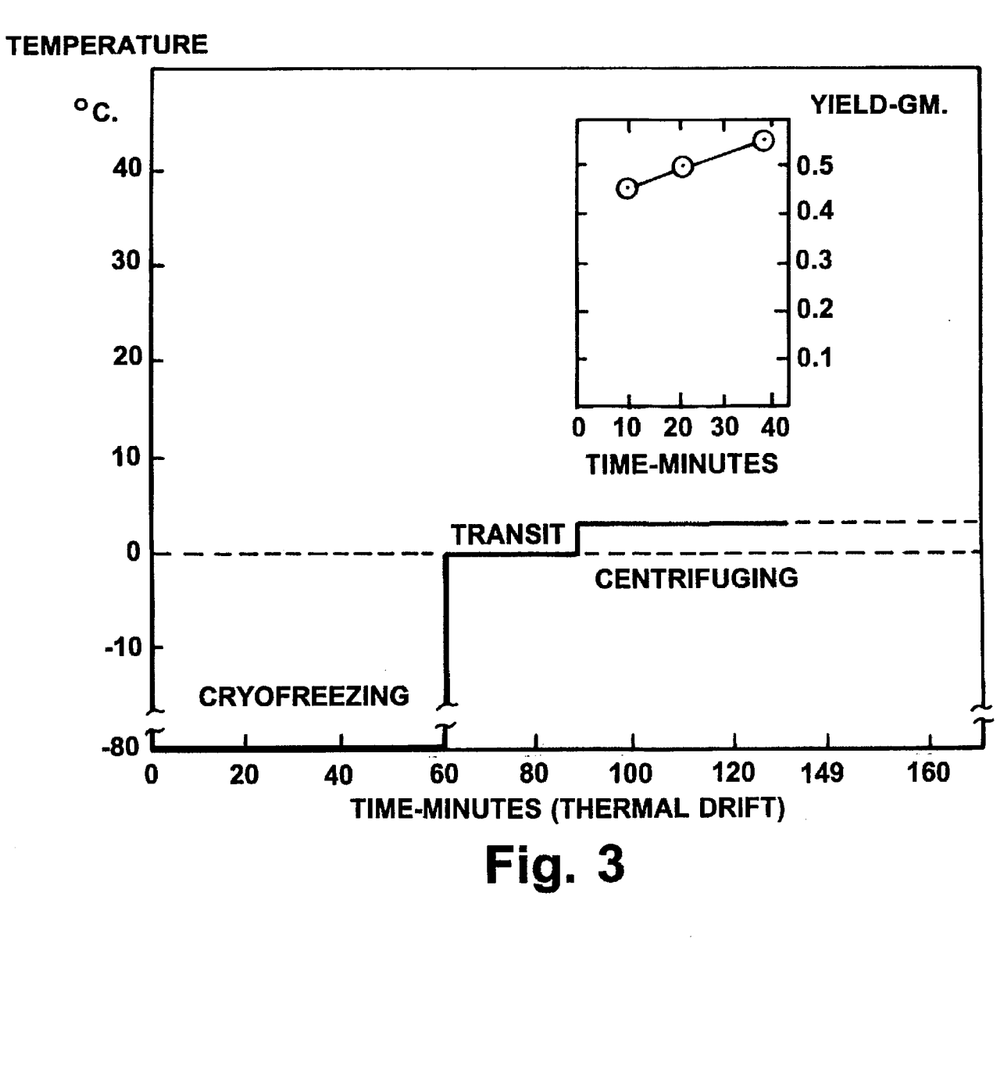
FIG. 3 shows a plot of thermal drift temperature versus time during the three process stages when thawing and centrifuging are performed concurrently.

For this Example, Table 2A and 2B summarize two thawing series, Series A with separate scheduled temperature-time thawing and centrifuging, and Series B which combines thawing with centrifugation. Numerous individual lots of human plasma, coded alphanumerically as FC-0XX, were obtained in most instances as fresh frozen plasma with varied storage periods up to several weeks at −20° C. or used direct from packed red cell separations. FIGS. 2 and 3 depict the overall process system typical for each of these two series along with related process yields of the respective concentrates.

A marked change takes place in the overall process efficiency not evident from any of the known prior art. This was discovered in Series A, in the accelerated thawing at 37° C., to reduce the prolonged 20 hour (Siedentop, 1985) or 12 hour (Spotnitz) thawing. Marked changes are also evident in Series B, by eliminating the separate accelerated thawing for controlled refrigeration above the solidus-liquidus equilibrium temperature. In this regard, analyses from Fraction I of Table 2A show that the productivity (i.e. yield ×solids) is increased progressively from 0.329 gm/100 ml plasma with thawing to complete liquidus state, i.e. with 0% icing, to 0.465 gm/100 ml plasma with 30% icing then reaching a maximum of 1.497 gm/100 ml plasma as the thawing is restricted to 90% or near 100%. Thus, a 4.5 fold enhancement of valuable fibrinogen and associated protein factors was attained. The thermal drift to the plasma is related to and dependent upon the surface:volume ratio plasma exposure in the solidus—liquidus transition at the controlled refrigeration during centrifugation. The efficiency of the cryofreezing method of preparing autologous fibrinogen concentrates can thus be reduced to near 2 hours or less for preemptive clinical preparations.

Specifically, the marked process improvement in further reducing the thawing time, with higher surface:volume ratio for the thermal drift; and combining thawing with the centrifuge stage is statistically summarized in Table 2A and 2B with regard to concentrate yield in grams, percent solids, and integrated process efficiency expressed as the concentrating ratio (×) over the initial plasma fibrinogen assay.

Series B maintained the equilibrium icing state for a longer period to as much as 40 minutes in the centrifuging stage for minimal redissolving of the cryoprecipitates, whereas with Series A accelerated 37° C. thawing, the icing is decreased to the liquidus state with substantial redissolving of the cryoprecipitates and decreased yields. Series B attained as high as 32% to 40% solids overall compared to 10.2% to 15.9% attained with Series A, again as a result of the diminished external thawing including that with the standby transfer time. Clearly the overall process thermal drift such as depicted in FIGS. 2 and 3, is regulated by the applied temperature-time thermal drift so as to terminate the de-icing to about 20% beyond which the redissolving of the plasma proteins can be expected to continue and decrease the yield, solids content, and concentrating ratio (×). By way of appraising the efficiency of the overall concentrating process of this invention, the overall clinical assay in the case of Series B with the concomitant thawing-centrifuging and controlled icing, provides as much as 20-fold protein content over the statistical mean (μ) native fibrinogen content in an average 250 ml unit of fresh frozen plasma

TABLE 2A

Summary of Accelerated Thawing Schedules and Combined Thawing Centrifugation

| Series A | | | | | Avg Ylds |
|---|---|---|---|---|---|
| Plasma Code | FC 039 | FC 042a | FC 042b | FC 043 | |
| Thaw min:°C. | 60:37 | 60:37 | 60:37 | 60:37 | |
| Transfer min:°C. | 47:RT | 21:RT | 21:RT | 42:0 | |
| CENTRIFUGATION FRACTION 1 | | | | | |
| Time (min) | 20 | 20 | 20 | 20 | — |
| Unit Vol (ml) | 9 | 9 | 9 | 9 | — |
| *% Icing | 0 | 0 | 0 | 30 | — |
| Yield (gm) | 0.171 | 0.146 | 0.267 | 0.322 | 0.227 |
| % Solids | — | — | 11.1 | 13.0 | 12.1 |
| **Conc. ratio | — | — | 20.9x | 24.5x | 22.7x |
| CENTRIFUGATION FRACTION 2 | | | | | |
| Time (min) | N/A | 40 | 40 | 40 | — |
| Unit Vol (ml) | | 9 | 9 | 9 | — |
| *% Icing | | 0 | 0 | 0 | — |
| Yield (gm) | | 0.177 | 0.362 | 0.275 | 0.271 |
| % Solids | | — | 10.2 | 14.5 | 12.5 |
| **Conc. ratio | | — | 19.2x | 27.3 | 23.5 |
| CENTRIFUGATION FRACTION 3 | | | | | |
| Time (min) | N/A | 60 | 60 | 60 | — |
| Unit Vol (ml) | | 9 | 9 | 9 | — |
| *% Icing | | 0 | 0 | 0 | — |
| Yield (gm) | | 0.189 | .330 | 0.272 | 0.264 |
| % Solids | | — | 10.6 | 15.9 | 13.3 |
| **Conc. ratio | | — | 20.0x | 30.0x | 25.0 |

*Visually estimated volume from a graded (100, 90, 80, 60, 40, 20, 10 and 0%) profile of internal ice plug.
**Based on universal (population mean) average 0.531 taken from the clinical average 531 mgm/dcl (Castillo).

TABLE 2B

Summary of Accelerated Thawing Schedules and Combined Thawing Centrifugation

| Series B | | | | | | | Avg Ylds |
|---|---|---|---|---|---|---|---|
| Plasma Code | FC 045 | FC 046 | FC 047b | FC 048 | FC 048b | FC 052 | |
| Thaw min | 36 | 25 | 34 | 25 | 25 | 27 | |
| °C. | 0 | 0 | 0 | 0 | 0 | 0 | |
| Transfer min °C. | N/A | N/A | N/A | N/A | N/A | N/A | N/A |
| CENTRIFUGATION FRACTION 1 | | | | | | | |
| Time (min) | 20 | 20 | 10 | 10 | 10 | 10 | — |
| Unit Vol (ml) | 9 | 9 | 9 | 9 | 9 | 9 | — |
| *% Icing | 50 | 80 | 100 | 100 | 80 | 90 | — |
| Yield (gm) | 0.434 | 0.434 | 0.332 | 0.389 | 0.397 | 0.452 | 0.407 |
| % Solids | 23.4 | 26.3 | 32.3 | 22.4 | 27.4 | 29.8 | 26.9 |
| **Conc. ratio | 44.3x | 49.5x | 60.8x | 42.2x | 51.6x | 56.1x | 59.6x |
| CENTRIFUGATION FRACTION 2 | | | | | | | |
| Time (min) | 40 | 40 | 20 | 20 | 20 | 20 | — |
| Unit Vol (ml) | 9 | 9 | 9 | 9 | 9 | 9 | — |
| *% Icing | 20 | 50 | 80 | 90 | 65 | 65 | — |
| Yield (gm) | 0.374 | 0.461 | 0.369 | 0.403 | 0.489 | 0.500 | 0.434 |
| % Solids | 20.4 | 24.7 | 29.4 | 36.9 | 23.4 | 26.3 | 26.9 |
| **Conc. ratio | 38.4 | 46.5x | 55.4x | 69.5x | 44.1x | 49.5x | 59.6 |
| CENTRIFUGATION FRACTION 3 | | | | | | | |
| Time (min) | 60 | 60 | 40 | 40 | 40 | 40 | — |
| Unit Vol (ml) | 9 | 9 | 9 | 9 | 9 | 9 | — |
| *% Icing | 10 | 15 | 50 | 45 | 20 | 30 | — |
| Yield (gm) | 0.378 | 0.463 | 0.406 | 0.467 | 0.383 | 0.559 | 0.443 |

TABLE 2B-continued

Summary of Accelerated Thawing Schedules
and Combined Thawing Centrifugation

| Series B | | | | | | | Avg Ylds |
|---|---|---|---|---|---|---|---|
| % Solids | 11.6 | 23.6 | 17.9 | 23.5 | 26.9 | 40.8 | 24.1 |
| **Conc. ratio | 21.8x | 44.4x | 33.7x | 44.2x | 50.7x | 76.8x | 45.3x |

*Visually estimated volume from a graded (100, 90, 80, 60, 40, 20, 10 and 0%) profile of internal ice plug.
**Based on universal (population mean) average 0.531 taken from the clinical average 531 mgm/dcl (Castillo).

EXAMPLE III

This example demonstrates the effect of increasing centrifugation as the third component of the engineering process for attaining shortened periods of time for the preemptive preparation of autologous fibrinogen concentrate for immediate, ready clinical needs. This example extends the concept of this invention based on minimized, regulated thawing at the solidus-liquidus stage of cryoprecipitation from the solid frozen state during the centrifugation.

In this example, the Du Pont Sorvall superspeed RC-5C centrifuge was used with the SM-24 Fixed 28° Angle Aluminum Rotor for 18×104 mm polypropylene tubes for 9 ml plasma units. This provides a surface:volume ratio of about 4.38:1 reciprocal cm, for higher thermal transfer efficiency compared to that of the 40 ml units used in previous Example I with approximately one-third 1.65:1 reciprocal cm ratio.

Cryoprecipitation. The routine −80° C. cryofreezing for 1 hour was used with quadruplicate groups of the 9 ml plasma units.

Thawing. The scheduled thawing such as used in Example I was eliminated and instead carried out concomitantly with the centrifugation process operation.

Centrifugation. A progressive series of 4000 (1710× g) 8000 (7910× g), and 12000 (17700× g) centrifuging was carried out with duplicate 9 ml units of plasma, a typical example of which was at the constant 4° C. for concomitant thawing from the solidus icing stage to the liquidus state at an extended range of time from 2 to 64 minutes.

At the completion of each time interval of centrifugation the duplicate plasma units were withdrawn. The residual icing content, just before decanting the supernatant spent plasma, was estimated visually as approximate percent volume for each progressive increment of centrifuging time. The residual icing is an important indicator of the solidus-liquidus equilibrium state and serves as a means for controlling the re-dissolving of associated proteins of lesser solubility than that of the higher molecular weight fibrinogen. Also with continued centrifugation after all the icing is gone, the redissolving continues with decreasing yield of the cryoprecipitate concentrates. It is therefore the practice to use incremental schedules of the combined thawing and centrifugation for adjusting the overall integrated process for whatever proportion of fibrinogen to associated plasma factors and proteins may be desired.

The results of this Series are summarized in Table 3 relating the Series of centrifuging incremental time schedules for each of the centrifuging RPM speeds. The refrigerating temperature was steady at the 4° C. setting in the case of the 4000 and 8000 RPM centrifuging, and drifted to 5° C. in the case of the 12000 RPM run. The latter is attributed to frictional rise in temperature due to higher internally circulating air speed. As the icing stage diminished with increasing melting into the liquidus stage, the yield increased to a maximum in each case, due to release of the frozen precipitate from the solidus ice stage, and then proceeded to decrease in yield with increasing time of centrifuging. The potentially useful lower molecular weight protein components notably the globulins and albumins can be retained with the fibrinogen concentrate or allowed to re-dissolve for succeeding concentration and separation by this invention. This complexity of on-going thermal drift with concomitant cryoprecipitation with sedimentation from the solidus stage to the re-dissolving at the liquidus stage will be made apparent in the ensuing Example IV.

Referring again to Table 3, the solids content in the case of the 4000 and the 8000 RPM series increases to 38.4% and 36.0%, respectively, while at 12000 RPM the expected similar level attained only 29.0% presumably due to the slight increase (4° C. to 5° C.) in temperature during the higher centrifuging RPM speed.

In summary, regarding to the overall process efficiency, Table 3 lists the concentrating ratio of the percent solids, determined by the water evaporative method described in Example II, to the universal plasma mean (μ) of 0.513% displaying a range of 32.6 times to 72.3 times the enhancement in the attained fibrinogen protein concentrates compared to the 5.6 times to 16.9 times range that would be attainable by the prolonged processes in the prior art. Apart from the valuable technical feature attaining superior high solids concentrate, the merit of reducing substantially the overall process time is in itself a surprising and, desirable innovation of major economic importance not only commercially but also in clinical cost effectiveness.

TABLE 3

Summary of Progressive Centrifugation RPM Speeds

| Process - Product Results | Centrifuge Speed RPM | xg | Centrifuge Time Phase Series - Minutes | | | | | |
|---|---|---|---|---|---|---|---|---|
| | | | 2 | 4 | 8 | 16 | 32 | 64 |
| Temperature (°C.) | 4000 | 1710 | — | — | 4 | 4 | 4 | 4 |
| | 6000 | 7910 | — | 4 | 4 | 4 | 4 | — |
| | 12000 | 17700 | (5) | (5) | (6) | — | — | — |
| % Residual Icing | 4000 | 1710 | — | — | solid | 95 | 90 | 80 |
| | 6000 | 7910 | — | solid | 95 | 90 | 80 | — |
| | 12000 | 17700 | 90 | 60 | 40 | — | — | — |
| Yields Avg (grams) | 4000 | 1710 | — | — | — | 0.389 | 0.465 | 0.430 |
| | 8000 | 7910 | — | — | 0.450 | 0.556 | 0.512 | — |
| | 12000 | 17700 | 0.504 | 0.571 | 0.456 | — | — | — |
| % Solids Content | 4000 | 1710 | — | — | — | 17.3 | 23.1 | 38.4 |
| | 8000 | 7910 | — | — | 24.0 | 23.7 | 36.0 | — |
| | 12000 | 17700 | 25.9 | 26.6 | 24.0 | — | — | — |
| Concentration Ratio | 4000 | 1710 | — | — | — | 32.6x | 43.5x | 72.3 |
| | 8000 | 7910 | — | — | 45.2x | 44.6x | 67.8x | — |
| | 12000 | 17700 | 48.8x | 50.1x | 45.2x | — | — | — |

EXAMPLE IV

This example relates to the biochemical analyses of a typical fibrinogen concentrate subject to repeated cryoprecipitation to recover the fibrinogen and associated proteins that may have redissolved during the preceding thawing and centrifugation. This aspect of the prior art has surprisingly been overlooked. The prolonged procedures of conventional processes in each of three principal processes, namely, cryoprecipitation, thawing, and centrifugation are believed to inadvertently discard a considerable proportion of available fibrinogen and the valuable associated proteins. In this example the supernatant of the first cryoprecipitated centrifugation was subject to a second repeated cryoprecipitation, thawing, and centrifugation of the retained supernatant.

Cryofreezing. A 40 ml unit of stored plasma fluid was placed in a 50 ml polypropylene tube providing a 1.65 surface:volume ratio for centrifuging in the International Refrigerated Centrifuge FP-2 in a horizontal swinging bucket preparing the first designated Fraction I concentrate. The same cryofreezing is repeated with the supernatants from the appropriate preceding centrifugations for preparing the corresponding Fractions II and III. The product analyses of the concentrates are summarized in Table 4.

Fraction I. Four tubes (Tube Nos. 1 to 4) of 40 ml plasma each were cryofrozen at −80° C. for 1 hour, thawed at 37° C. for 30 minutes and then centrifuged at 2000 RPM (1420× g) for 30 minutes yielding an average of 1.171 gm of fibrinogen concentrate with 15.1 percent solids per 40 ml plasma units amounting to a process efficiency, in terms of concentrating ratio, of 28.5× based on the universal mean fibrinogen assay of 0.531% in the initial plasma. The concentrate from this first centrifugation is designated Fraction I fibrinogen concentrate for the ensuing biochemical analyses of the protein by polyacrylamide gel electrophoreses.

Fraction II. The four supernatants from the preceding Fraction I were similarly repeated for cryofreezing, thawing, and centrifuging. As indicated in Table 4, the second Fraction II surprisingly revealed that an additional yield of concentrate averaging 0.577 grams, or 33.4% of the two combined Fractions, as shown by the ensuing electrophoreses patterns, was obtained with a significantly higher fibrinogen content approaching purer form. In this Example the cryoprecipitates separated fully to depletion from the plasma. The process efficiency in terms of concentration ratio in Fraction II averaged 27.1× and comparable to that of Fraction I.

Incidental to this second yield of fibrinogen concentrate, it is noteworthy that the first Fraction I thawing incurred fractional re-dissolving of cryoprecipitate during the thermal drift time from the solidus to liquidus transition which was re-cryoprecipitated in Fraction II. The ensuing protein analyses indicate that regulated thawing with two or more cryoprecipitation phases provides a significant and novel modification of overall process system for fractional-separation of desired proteins based on their selected solubilities at the thawing phase not obvious in the prior art.

Fraction III. The supernatant from the preceding Fraction II was similarly processed from cryoprecipitation producing concentrates that were barely discernable. The accumulated or combined centrifuging time of 1.0 hour depleted substantially the available cryoprecipitable proteins of the plasma, another feature of this invention not evident or made obvious in the prior art.

Figure 4:
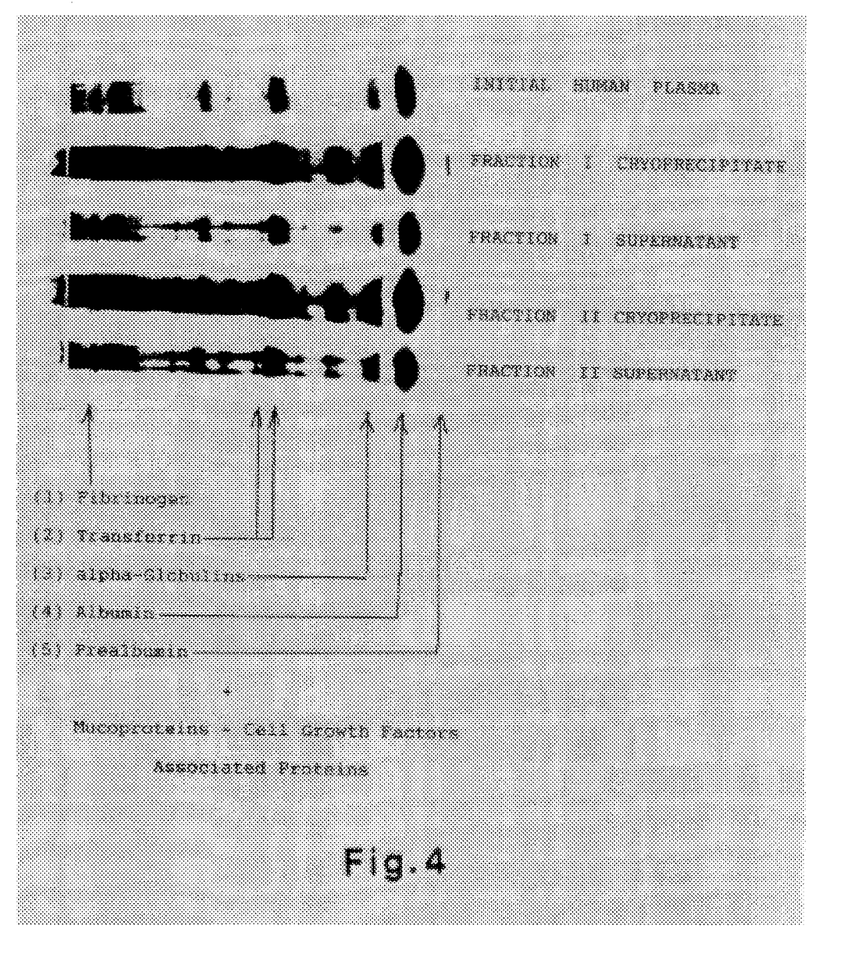
FIG. 4 displays the characteristic distribution of proteins in the fibrinogen concentrate from polyacrylamide gel electrophoresis.

Protein Analyses. The Fraction I and II concentrates along with the initial plasma and the supernatant spent plasma were made up in 1% dilutions and subjected to analyses run in 7% polyacrylamide electrophoresis gel. FIG. 4 provides the identity of the proteins indexed numerically from the high molecular weight fibrinogen of about 400,000 daltons, to the lower molecular weight and more soluble albumins down to about 60,000 daltons. Included in the range are numerous glycoproteins of intermediate molecular weights, particularly mucoproteins (bioadhesives), transferrin, cell growth factors known to be separable by chromatography (Holmes, 1967).

Based on measured band areas of the electrophoretic patterns such as shown in FIG. 4, specifically that of the fibrinogen and albumin, Table 5 summarizes the integrated band areas for these two protein components along with the respective fibrinogen/albumin ratio (quotient) thereby revealing that the Fractional (I, II, etc.) phases of centrifuging to depletion produced increasing ratios of the fibrinogen/albumin approaching high purity of fibrinogen. As indicated in Table 5, commencing with the initial fibrinogen:albumin ratio of 0.77 (actually the quotient of the ratio 0.77:1) of the initial plasma, the first Fraction I concentrate doubles the initial ratio to 1.61. After the second cryoprecipitation from the decanted supernatant Fraction II, the fibrinogen:albumin ratio was enhanced to the ratio of 40.1 demonstrating the potential for producing a broad range of protein compositions of cryoprecipitated concentrates for innumerable blood products that can be selectively cryoprecipitated.

TABLE 4

Preparation of Cryoprecipitates for Analyses of Protein Distributions from Multi-Stage Cryoprecipitation

| | TUBE NUMBER | | | | |
|---|---|---|---|---|---|
| | 1 | 2 | 3 | 4 | Average |
| FRACTION I | | | | | |
| Yield grams | 1.122 | 1.387 | 1.287 | 0.888 | 1.171 |
| solids % | 14.9* | 14.1 | 16.1 | 15.3 | 15.1 |
| conc ratio (x) | 28.1 | 26.6 | 30.3 | 28.8 | 28.5 |
| FRACTION II | | | | | |
| Yield grams | 0.401 | 0.877 | 0.563 | 0.467 | 0.577 |
| solids % | 16.3* | 14.4 | 13.8 | 13.1 | 14.4 |
| conc ratio (x) | 30.7 | 27.1 | 26.0 | 24.7 | 27.1 |
| FRACTION III | | | | | |
| Yield grams | 0.010 | N/A | N/A | N/A | N/A |
| Solids % | N/A | N/A | N/A | N/A | N/A |
| conc ration (x) | N/A | N/A | N/A | N/A | N/A |

*Used for FIG. 4 gel electrophoresis.

TABLE 5

Protein Distribution Ratios of Fibrinogen Concentrates from Polyacrylamide Gel Electrophoresis

| Product | Fibrinogen | Albumin | Fibrinogen Albumin |
|---|---|---|---|
| Initial Plasma Fraction I | 0.982 | 1.28 | 0.77 |
| Conc | 2.06 | 1.28 | 1.61 |
| Sup | 1.78 | 1.33 | 1.34 |

TABLE 5-continued

Protein Distribution Ratios of Fibrinogen Concentrates from Polyacrylamide Gel Electrophoresis

| Product | Fibrinogen | Albumin | Fibrinogen Albumin |
|---|---|---|---|
| Fraction II | | | |
| Conc | 1.08 | 0.027 | 40.1 |
| Sup | 1.10 | 1.21 | 0.90 |

Conc = Concentrate; Sup = Supernatant. Band masses seen in FIG. 4 were determined from integrated band area on test samples run at their respective solids contents.

EXAMPLE V

Mammalian plasma other than the human also serve as important sources of plasma and serum proteins. Innumerable proteins and peptides derived from bovine plasma are used in clinical applications and even as the plasma itself in tissue culture especially in cell growth and in biological research. The cryoprecipitive separation and concentration process of this invention is equally and readily applicable to the integrated process of this invention to provide a commercial source of fractionated proteins and peptides.

In this Example, a 450 ml unit source of fresh bovine (cow) blood drawn into 75 ml ACD solution, U.S.P. Formula, was processed initially for the separation of the erythrocytes by centrifuging at 2000 RPM at 15° C. for 1 hour in 50 ml polypropylene tubes from which approximately 35 ml of plasma was decanted. The processing followed substantially the same cryoprecipitation and combined thawing centrifuging at 4° C. at the time intervals from 2 to 64 minutes as described in preceding Example III using the same surface:volume ratio of 4.65:1 reciprocal cm, with the 9 ml polypropylene centrifuging tubes.

The corresponding yields and percent solids are summarized in Table 6 based on the processing temperature-time experimental design matrix shown in Table 3. The yields in grams of bovine fibrinogen concentrates are fairly comparable to that of human fibrinogen concentrates in Example III as are the solids content and concentrating ratios. Protein analyses based on polyacrylamide gel electrophoresis displayed a broad range of proteins from the high molecular weight fibrinogen and α2-macroglobulin, to the low molecular weight albumins depending on the incremental centrifuge time phases and repeated fractional cryofreezing precipitations to the centrifugation. With the multi-faceted matrix array of process variables in relation to the protein distribution analyses it is possible to adjust and regulate the engineering process variables to separate in high degree of purity any one the selected components protein components associated with various indigenous fibrinogen factors.

TABLE 6

Summary of Progressive Centrifugation RPM Speeds

| Process - Product Results | Centrifuge Speed | | Centrifuge Time Phase Series - Minutes | | | | | |
|---|---|---|---|---|---|---|---|---|
| | RPM | xg | 2 | 4 | 8 | 16 | 32 | 64 |
| Temperature (°C.) | 4000 | 1710 | — | — | — | 4 | 4 | 4 |
| | 6000 | 7910 | — | — | — | 6 | 6 | 6 |
| | 12000 | 17700 | — | 4 | 4 | 4 | — | — |
| % Residual Icing | 4000 | 1710 | — | — | solid | 95 | 90 | 90 |
| | 6000 | 7910 | — | — | solid | 95 | 65 | 0 |
| | 12000 | 17700 | solid | 95 | 90 | 85 | — | — |
| Yields Avg. (grams) | 4000 | 1710 | — | — | — | 0.332 | 0.523 | 0.420 |
| | 8000 | 7910 | — | — | — | 0.461 | 0.451 | 0.508 |
| | 12000 | 17700 | — | 0.459 | 0.535 | 0.666 | — | — |

TABLE 6-continued

Summary of Progressive Centrifugation RPM Speeds

| Process - Product Results | Centrifuge Speed | | Centrifuge Time Phase Series - Minutes | | | | | |
|---|---|---|---|---|---|---|---|---|
| | RPM | xg | 2 | 4 | 8 | 16 | 32 | 64 |
| % Solids Content | 4000 | 1710 | — | — | — | 19.0 | 21.9 | 20.9 |
| | 8000 | 7910 | — | — | — | 22.7 | 21.0 | 21.5 |
| | 12000 | 17700 | — | 33.6 | 24.1 | 25.1 | — | — |
| Concentration | 4000 | 1710 | — | — | — | 37.1x | 42.7x | 40.8x |
| Ratio | 8000 | 7910 | — | — | — | 43.9x | 41.0x | 42.0x |
| | 12000 | 17700 | — | 65.6x | 47.0x | 49.0x | — | — |

EXAMPLE VI

The process of the present invention is equally applicable to plasma like substances, bearing high molecular weight soluble and colloidal proteins and peptides, that pervade throughout the living systems not only hematological but also in tissue and cells of innumerable organs and organisms. This Example provides a typical exploratory example for preparing concentrates from protoplasmic cytoplasm.

An accumulated harvesting of a series of 15 to 30 day cultured human abdominal trypsinized fascia cells were collected to a volume of 1.8 ml in a 50 ml polypropylene tube and dispersed in 14 ml Ringers lactate with mild vortexing. The resuspended dispersed cells were diluted with Ringers lactate to 18 ml, sonicated to disrupt the cellular walls, and centrifuged at 2000 RPM at ambient room temperature for 60 minutes to remove the cellular debris.

The clear supernatant was placed in two equal portions in a 10 ml polypropylene tube and cryofrozen at $-80°$ C. for 1 hour. The cryofrozen supernatant was thawed during centrifuging at $4°$ C. in the RC-5C centrifuge in the angular rotor at 12000 RPM for 32 minutes with approximately 20% residual icing yielding approximately 0.120 grams of white mucous like product with a strong biuret reaction gram characteristic of proteins and peptides substantial portion of which melts at room temperature but remain solid in storage at $-20°$ C. The product is intended for scaled up production of potential cell growth factors.

The three component processes of the overall integrated engineering system, designed to attain the degree of enhancement of the fibrinogen or fibrinogen protein concentrate involves controlling the thermal drift at each of three process stages and thermal transfer in cryofreezing and in subsequent thawing, in a separate schedule or concomitantly with centrifugation. The latter controls the concomitant but competitive mechanisms of precipitation during de-icing and resolubilization at each temperature-time phase. This is made evident in several instances of prolonged thawing centrifugation with increasing yields followed by decreases. Such being evident, ordinary extensions of the critical time-temperature phases can lead to inadequate or decreased yields of the final product. Also in this invention, each of these three process steps is accorded consideration of the surface to volume ratio as a controlling or dominant factor of thermal-time transfer in the regulation of the de-icing measured by the residual percentage of icing.

Considering these Examples in their integrated entirety, the process engineering system for producing enhanced high solids of cryoprecipitated fibrinogen concentrates can be equated in terms of the following descriptive expression:

$$[\text{Cryofreezing}]^X \times [\text{Thawing}]^Y \times [\text{Centrifugation}]^Z$$
$$T \times t \times S/V \quad\quad T' \times \Delta H \quad\quad T'' \times t \times xg$$

where T, T', and T" are the imposed environmental temperatures as provided in the various Examples, t represents the time, S/V the surface to volume ratio, $\Delta H$ the heat transfer gradient or rate, and $\times$ g the gravitational force for each of the three processes with their characteristic controlling exponents X, Y and Z directed to the desired biochemical components of the enhanced fibrinogen protein or fibrinogen concentrate. As discussed for each Example, the kinetic aspects of this equated expression can be applied to small clinical laboratory lots, especially for autologous needs, avoiding risks of viral contamination from non-specific donor, and for large commercial scale production of the fibrinogen and valuable plasma proteins, usually in flat plastic blood collection containers or bags providing surface to volume ratios in the range of from about 1.00 to about 4.50 depending upon the contained plasma volume.

While the concept and examples as discussed herein relate to plasma normally produced and processed, the process of the present invention is applicable to any mammalian plasma or cell plasma or any modifications thereof with supplemental additions and inclusions of various kinds. The foregoing process of the present invention and illustrative examples are directed toward the characteristic feature of plasma, its contained fibrinogen. Conventional processes preempt this feature of plasma by dialyzing, heat inactivating, delipidizing, filtering, and/or irradiating plasma.

While the process of the present invention is herein described for use with conventional centrifuge tubes, the process is applicable to closed systems, against contamination, of conventional apheresis of blood components using flat plastic bags with satellite collecting sections.

Various modifications of the invention in addition to those shown and described herein will be apparent to those skilled in the art from the foregoing description. Such modifications are also intended to fall within the scope of the appended claims.

What is claimed:

1. A process for producing a fibrinogen concentrate from mammalian plasma comprising:

a. freezing said plasma to a temperature of at most about $-20°$ C. for less than four hours in a container having a surface to volume ratio of about 4.38:1 to about 1.65:1 reciprocal centimeters, thereby producing frozen plasma;

b. thawing said frozen plasma at a temperature of at least about $4°$ C. for a time sufficient to attain from about 5% to about 95% residual icing, thereby producing thawed plasma; and c. centrifuging said thawed plasma to produce a supernatant and a fibrinogen concentrate having about 6% to about 44% solids content by weight.

2. The process of claim 1 wherein freezing is performed at a temperature of about −20° C. to about −120° C.

3. The process of claim 1 wherein freezing is performed for a time of at least about 0.5 hours.

4. The process of claim 1 wherein said thawing is performed at a temperature of about 4° C. to about 10° C.

5. The process of claim 1 wherein said thawing is performed for a time of about 1 hour.

6. The process of claim 1 wherein thawing is performed for a time sufficient to attain from about 30% to about 40% residual icing.

7. The process of claim 1 wherein centrifuging produces a fibrinogen concentrate having about 12% solids content by weight.

8. The process of claim 1 wherein centrifuging produces a fibrinogen concentrate having about 24% solids content by weight.

9. The process of claim 1 wherein centrifuging is performed at a gravitational force of about 1450× g to about 8000× g.

10. The process of claim 1 wherein centrifuging is performed for a time of about 1 hour.

11. The process of claim 1 wherein thawing and centrifuging are performed simultaneously.

12. The process of claim 1 wherein said mammalian plasma is selected from the group consisting of human, bovine, porcine, and ovine plasma.

13. The process of claim 1 wherein said mammalian plasma is selected from the group consisting of autologous and allogenic plasmas.

14. The process of claim 1 repeated with said supernatant resulting from centrifuging said thawed plasma.

15. A process for producing a fibrinogen concentrate from cell cytoplasm containing fibrinogen comprising:
   a. freezing said cytoplasm to a temperature of at most about −20° C. for less than four hours in a container having a surface to volume ratio of about 4.38:1 to about 1.65:1 reciprocal centimeters, thereby producing frozen plasma;
   b. thawing said frozen plasma at a temperature of at most about 4° C. for a time sufficient to attain from about 5% to about 95% residual icing, thereby producing thawed cytoplasm; and
   c. centrifuging said thawed cytoplasm to produce a supernatant and a fibrinogen concentrate having about 6% to about 44% solids content by weight.

16. A process for producing fibrinogen concentrate from mammalian plasma comprising:
   a. freezing said plasma to a temperature of at most about −20° C. for less than four hours in a container having a surface to volume ratio of about 4.38:1 to about 1.65:1 reciprocal centimeters, thereby producing frozen plasma;
   b. thawing said frozen plasma at a temperature of at least 4° C. for a time sufficient to attain from about 5% to about 95% residual icing, thereby producing thawed plasma;
   c. centrifuging said thawed plasma to produce a first supernatant and a first fibrinogen concentrate having about 6% to about 44% solids content by weight;
   d. freezing said first supernatant to a temperature of at most about −20° C. for less than four hours in a container having a surface to volume ratio of about 4.38:1 to about 1.65:1 reciprocal centimeters, thereby producing frozen first supernatant;
   e. thawing said frozen first supernatant at a temperature of at most about 4° C. for a time sufficient to attain from about 5% to about 9.5% residual icing thereby producing thawed first supernatant;
   f. centrifuging said thawed first supernatant to produce a second supernatant and a second fibrinogen concentrate having about 6% to about 44% solids content by weight.

17. The process of claim 16 wherein said process is repeated for a plurality of times such that a plurality of supernatants and a plurality of concentrates are produced.

18. The process of claim 17 wherein said plurality of concentrates are combined.

* * * * *